United States Patent [19]

Matsuo

[11] Patent Number: 4,827,908
[45] Date of Patent: May 9, 1989

[54] ENDOSCOPIC APPARATUS

[75] Inventor: Satoshi Matsuo, Ohtawara, Japan

[73] Assignee: Kabushiki Kaisha Toshiba, Kawasaki, Japan

[21] Appl. No.: 174,983

[22] Filed: Mar. 29, 1988

[30] Foreign Application Priority Data

Mar. 30, 1987 [JP] Japan .................................. 62-74391

[51] Int. Cl.[4] .............................................. A61B 1/04
[52] U.S. Cl. .......................................... 128/6; 358/98
[58] Field of Search ................................ 128/6; 358/98

[56] References Cited

U.S. PATENT DOCUMENTS 4,667,230  5/1987  Arakawa et al. ..................... 358/98
4,774,568  9/1988  Matsuo ................................. 358/98

Primary Examiner—Leo P. Picard
Attorney, Agent, or Firm—Foley & Lardner, Schwartz, Jeffery, Schwaab, Mack, Blumenthal & Evans

[57] ABSTRACT

An endoscopic apparatus in which a scope having an image-pick up element at an end thereof can be selected and exchanged comprises a device for recognizing scope identification information provided to the scope in the attaching state of the scope; and a device for adjusting a change of the optical characteristics with respect to an output of the image pick-up element based on the scope identification information recognized by the recognizing device.

10 Claims, 5 Drawing Sheets

ENDOSCOPIC APPARATUS

The present invention relates to an endoscopic apparatus having a scope disposing therein a charge coupled device at an end thereof and suitably selected and exchanged.

BACKGROUND OF THE INVENTION

In a conventional endoscopic apparatus of this kind, in particular, in the case of a color electronic endoscopic apparatus of a simultaneously operating system, ununiform components are added to a converted output of a charge coupled device (CCD) by ununiformity of the optical characteristics due to light source, light guide fiber, lens, a combination thereof, or ununiformity of the spectral transmission characteristics of a color filter attached to the entire surface of the CCD, and the spectral sensitivity characteristics of the CCD, thereby deteriorating the reproducibility of the color. To solve this problem, the conventional apparatus has a signal processing circuit disposed in an apparatus's body separated from a scope and adjusting the color in order to remove the adverse effects due to the ununiform components.

A color electronic endoscopic apparatus of a field sequential system has no color filter attached to a front surface of the CCD, but has three color filters disposed on a light source side so that it is possible to generate ununiformity. Accordingly, even when the field sequential system is used, a signal processing circuit for adjusting the color is disposed in the apparatus's body separated from the scope, as well as in the case of the above simultaneously operating system.

However, since the ununiformity of the optical characteristics of respective scopes to be exchanged are respectively different from each other, the color must be adjusted by the signal processing circuit every time when a new scope is attached to the apparatus's body and is used.

In the conventional electronic endoscopic apparatus of this kind, after the scope is attached to the apparatus's body, the color must be adjusted by the signal processing circuit to remove the adverse effects due to the ununiformity, while examining the situations of the ununiformity of the optical characteristics caused by the scope itself. Accordingly, the adjustment of the color is complicated, and it often takes a long time to adjust the color so as to have a high color reproducibility.

SUMMARY OF THE INVENTION

To solve the problems mentioned above, an object of the present invention is to provide an endoscopic apparatus for performing the adjustment of the color having a high reproducibility immediately after a scope is attached to the apparatus's body.

With the above object in view, the present invention resides in an endoscopic apparatus in which a scope having an image pick-up element at an end thereof can be selected and exchanged, said apparatus comprising means for recognizing scope identification information provided to the scope in the attaching state of the scope; and means for adjusting a change of the optical characteristics caused by the scope itself and a light source with respect to an output of the image pick-up element based on the scope identification information recognized by the recognizing means.

In such a construction of the present invention mentioned above, when the scope is attached to the apparatus's body, the scope identification information indicative of the scope are recognized by the recognizing means, and the change of the optical characteristics caused by the attached scope itself and the light source can be automatically adjusted on the basis of the recognized results.

BRIEF DESCRIPTION OF THE DRAWINGS

The present invention will be more apparent from the following description of the preferred embodiments thereof in conjunction with the accompanying drawings in which.

DETAILED DESCRIPTION OF THE PREFERRED EMBODIMENTS

The preferred embodiments of an endoscopic apparatus in the present invention will now be described in detail with reference to the accompanying drawings.

Figure 1:
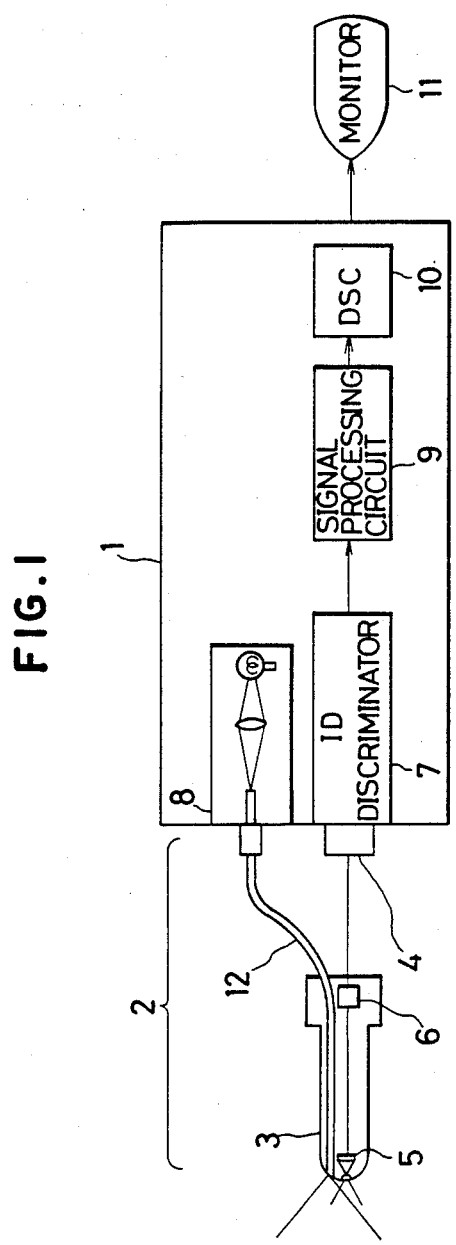
FIG. 1 is a block view schematically showing an electronic endoscopic apparatus in an embodiment of the present invention.

FIG. 1 schematically shows an embodiment of an electronic endoscopic apparatus of the present invention.

In the electronic endoscopic apparatus in this embodiment, a scope 2 can be attached and detached from an apparatus body 1, and is suitably selected from any one of forward-looking and side-looking scopes for upper gastrointestine for example, and L-size and M-size scopes for large intestine, etc., which are suitably exchanged for use.

The scope 2 is provided with a scope body 3 and a main connector 4 electrically connected to the apparatus body 1. The scope body 3 has therein a CCD 5 including a color filter and a drive/receiving circuit 6. The main connector 4 has an unillustrated mechanical structure for providing scope identification information(which is called scope ID in the following description) determined so as to correct all the optical characteristics of CCD 5 including a light guide 12, a lens of a light source described later, and a color filter.

The apparatus body 1 has a signal processing circuit 9 for adjusting a change of the optical characteristics caused by the scope itself and a light source 8 with respect to a converted output of the CCD 5 based on the discriminated results of the scope ID by an ID discriminator 7 for discriminating the scope ID supplied to the main connector 4, when the scope 2 is attached and electrically connected to the apparatus body 1 through the main connector 4. The apparatus body 1 further has a digital scan converter(which is called DSC in the following description) 10 for memorizing an image, inverting the image left and right, and controlling the image display. The light source 8 is constructed so as to guide light of a lamp 8a to the light guide 12 through a lens 8b. Reference numeral 11 designates a monitor display device for CRT, etc.

In the apparatus mentioned above, the signal processing circuit 9 adjusts the change of the optical characteristics in the converted output of the CCD 5 as follows.

The adjustment of the change of the optical characteristics is to adjust a color of an image by changing the hue and saturation of the image, which is performed by using the following two methods roughly.

A first method is the one for adjusting the color of the image by using red, green and blue(RGB) signals, and brightness and color difference(which is called Y/color difference in the following description) signals, which are called component signals.

A second method is the one for adjusting the color of the image at the stage of a modulated signal provided by modulating a sine wave at 3.58 MHz for example which is called a subcarrier.

In the first method, the relation between the RGB and Y/color difference signals is given by the following equation.

$$\begin{pmatrix} R-Y \\ B-Y \\ Y \end{pmatrix} = \begin{pmatrix} 0.70 & -0.59 & -0.11 \\ -0.30 & -0.59 & 0.89 \\ 0.30 & 0.59 & 0.11 \end{pmatrix} \begin{pmatrix} R \\ G \\ B \end{pmatrix} \quad (1)$$

where $(R-Y)$ and $(B-Y)$ each are respectively one of the color difference signals, and the color difference signal is a generic name of these two signals.

The relation between the RGB and Y/color difference signals is provided by equation (1), and the method for adjusting the image color will next be described with the Y/color difference as an example.

Figure 2:
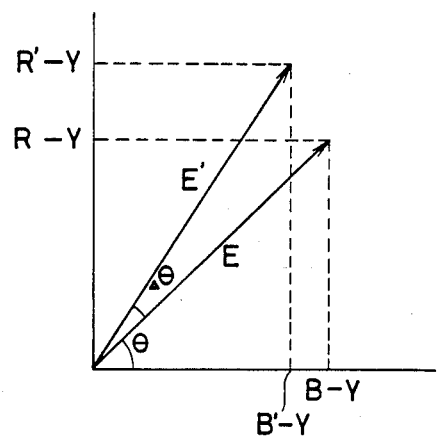
FIG. 2 is a view showing the relation between a color vector and a component signal.

As shown by FIG. 2, when a color vector indicated by E is changed to E', the following equation is given.

$$E = \{(R-Y)^2/k_1^2 + (B-Y)^2/k_2^2\}^{\frac{1}{2}} \quad (2)$$

$$\theta = \tan^{-1}(k_2/k_1 \times (R-Y)/(B-Y)) \quad (3)$$

where $K_1 = 1.14$, and $K_2 = 2.03$.

As shown in FIG. 2, when the hue is corrected by $\Delta\theta$, and the color vector E is corrected to E', $(R'-Y)$ and $(B'-Y)$ are calculated by the following equations:

$$E' = K_3 E$$

$$\theta = \Theta + \Delta Q$$

Accordingly, $$\begin{aligned}(R'-Y) &= 1.14 \, E' \sin(\theta + \Delta\theta) \\ &= K_1 K_3 E \sin(\theta + \Delta\theta) \\ &= K_1 K_3 E \{\sin\theta\cos\Delta\theta + \cos\theta\sin\Delta\theta\} \\ &= k_1 K_3 [\{(R-Y)/k_1\}\cos\Delta\theta + \\ &\quad \{(B-Y)/k_2\}\sin\Delta\theta\end{aligned} \quad (4)$$

$$\begin{aligned}(B'-Y) &= 2.03 \, E' \cos(\theta + \Delta\theta) \\ &= K_2 K_3 E \cos(\theta + \Delta\theta) \\ &= K_2 K_3 E \{\cos\theta\cos\Delta\theta - \sin\theta\sin\Delta\theta\} \\ &= k_2 K_3 [\{(B-Y)/k_2\}\cos\Delta\theta - \\ &\quad \{(R-Y)/k_1\}\sin\Delta\theta\end{aligned} \quad (5)$$

Equations (4) and (5) are rewritten by the following equation:

$$\begin{pmatrix} R'-Y \\ B'-Y \end{pmatrix} = k_3 \begin{pmatrix} \cos\Delta\theta & (K_1/k_2)\sin\Delta\theta \\ -(k_2/k_1)\sin\Delta\theta & \cos\Delta\theta \end{pmatrix} \begin{pmatrix} R-Y \\ B-Y \end{pmatrix} \quad (6)$$

Since equation (6) does not include $\theta$, the change shown in FIG. 2 can be performed by the same method with respect to all the hue.

Figure 3:
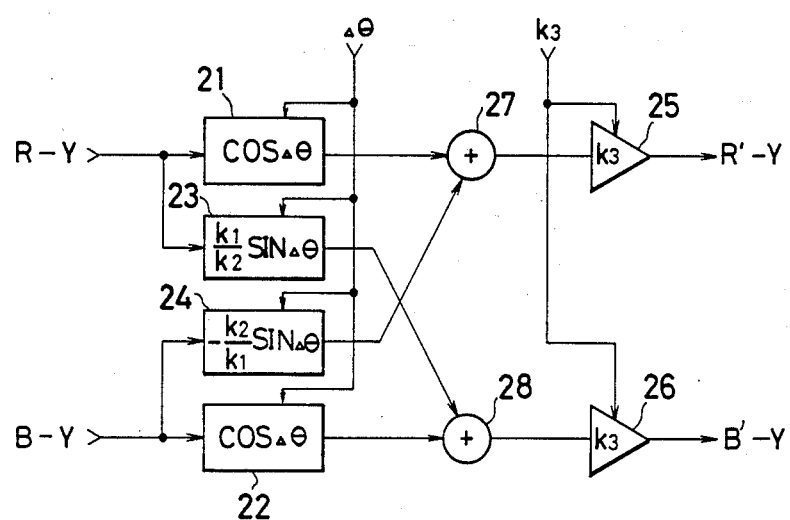
FIGS. 3 and 4 are block views showing the construction of main portions of a signal processing circuit.

A circuit block of equation (6) can be written as in FIG. 3.

In FIG. 3, reference numerals 21 to 26 designate a multiplicating circuit and reference numerals 27 to 28 designate an adding circuit.

By using the circuit shown in FIG. 3 as a unit, as shown in FIG. 2, the color vector having an arbitrary hue can be changed by arbitrary amount and angle thereof.

Figure 4:
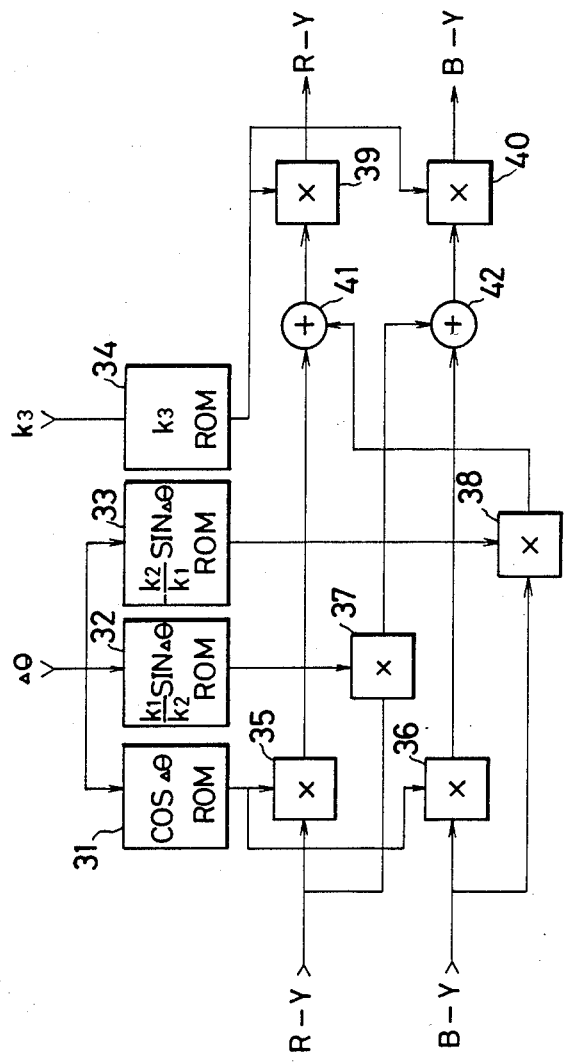

In FIG. 3, the sine and cosine $\Delta\theta$ functions shown by a rectangular shape are related to the change of the hue, and the $k_3$ functions shown by a triangular shape are related to the saturation. The image color can be adjusted by controlling these $\Delta\theta$ and $k_3$ functions from the exterior of the apparatus. A concrete method is used to adjust the image color by using a voltage-gain variable amplifier for the $\Delta\theta$ and $K_3$ functions shown by the rectangular and triangular shapes in FIG. 3. There is also another color adjusting method by using ROMs 31 to 34, multiplicating circuits 35 to 40 and adding circuits 41 and 42 as shown by FIG. 4 after converting a color difference signal to a digital signal. In these methods, it is necessary to generate voltages or addresses with respect to $\Delta\theta$ and $k_3$. These voltages or addresses are different from each other every scope as described before.

Accordingly, when the scope has identification(ID) information and the voltages and addresses corresponding to the ID information are generated, the circuit shown by FIG. 3 or 4 can be controlled from the exterior of the apparatus. The ID information of the scope are determined so as to correct all the optical characteristics of the CCD including a light guide, a lens and a color filter. Accordingly, when the ununiformity of a light source is prevented by a certain method, the reproducibility of the color can be correctly provided by the method mentioned above.

Figure 5:
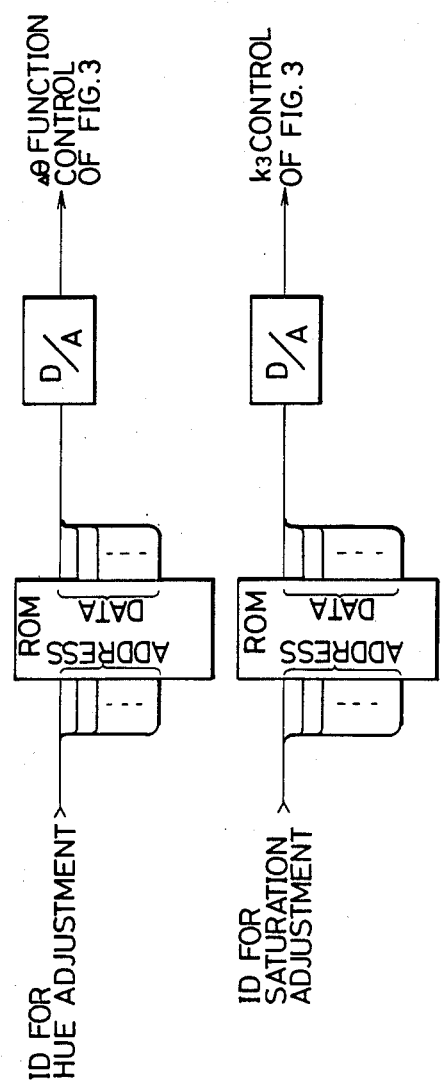
FIG. 5 is a view showing an example in which a control signal is generated from scope identification information.

FIG. 5 shows an example for generating a control signal by the scope ID. The ID information composed of a plurality of bits in the scope are used as addresses of ROMs, and data for correcting the ID information written in the ROMs in advance are read out. The readout digital data are inputted to D/A converters to obtain corresponding analog voltages. The analog voltages are supplied to the voltage-gain variable amplifier of FIG. 3, and the hue and saturation can be controlled by controlling the gain of the voltage-gain variable amplifier.

In the circuit of FIG. 4, the scope ID information may be directly inputted to ROMs for the $\Delta\theta$ and $k_3$ functions as addresses, but the ROMs shown in FIG. 5 may be disposed between the scope and the function ROMs.

In the above embodiment, a plurality of bits are used as scope ID, but a microprocessor or a dedicated control circuit may be disposed within the scope to output ID information as a serial signal.

Accordingly, when the scope 2 is attached and electrically connected to the apparatus body 1 through the main connector 4, the signal processing circuit 9 can adjust a change of a converted output of CCD 5 due to the ununiformity of the optical characteristics generated by the attached scope 2 and the light source 8 based on the discriminated results of the ID discriminator 7.

A video signal processed and obtained by the signal processing circuit 9 is transmitted to a monitor display device 11 through DSC 10 so that the reproducibility of the image color can be correctly provided on the screen of the monitor display device 11 immediately after the scope 2 is attached to the apparatus body 1.

Figure 6:
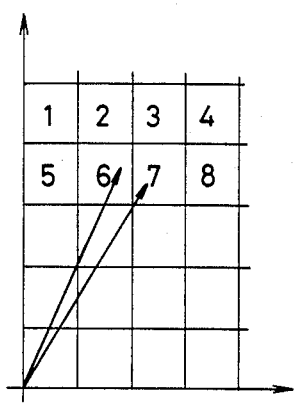
FIG. 6 is a view showing in which section the scope ID is located among a plurality of sections.

Further, as shown in FIG. 6, when a discriminating signal indicating in which section the scope ID is located among a plurality of sections 1, 2, 3, --- is outputted, and the data of the discriminating signal are stored in a ROM, and are outputted by the ROM to the circuit of FIG. 3 for the color difference $\Delta\theta$ and $k_3$ functions, the change of the optical characteristics due to a plurality of scopes different from each other can be automatically adjusted rapidly.

Figure 7:
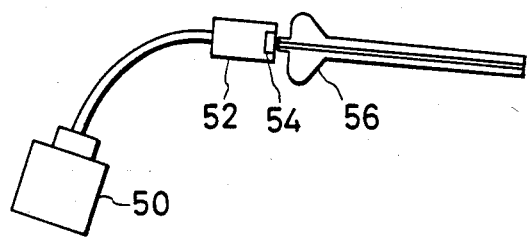
FIG. 7 is a view showing an embodiment of the endoscopic apparatus in which an image pick-up device provided with a CCD can be detached from a fiber scope.

FIG. 7 shows the structure of an endoscopic apparatus in which an image pick-up device 52 such as a camera connected to an apparatus body 50 and provided with a CCD 54 can be exchanged with respect to a scope 56. The present invention can be also applied to such a structure of the endoscopic apparatus.

As mentioned above, in an endoscopic apparatus of the present invention, when a scope is attached to the apparatus body, scope ID information are recognized, and a change of the optical characteristics due to the scope and a light source can be immediately adjusted on the basis of the recognized results, thereby providing the high reproducibility of the image color.

What is claimed is:

1. An endoscopic apparatus in which a scope having an image-pick up element at an end thereof can be selected and exchanged, said apparatus comprising:
   means for recognizing scope identification information provided to the scope in the attaching state of the scope; and
   means for adjusting a change of the optical characteristics with respect to an output of the image pick-up element based on the scope identification information recognized by the recognizing means.

2. An endoscopic apparatus as claimed in claim 1, wherein the change of the optical characteristics is caused by the scope itself and a light source for irradiating the scope.

3. An endoscopic apparatus as claimed in claim 1, wherein said adjusting means comprises a signal processing circuit for adjusting the change of the optical characteristics with respect to the output of the image pick-up element based on the discriminated results of the scope by a discriminator for discriminating the scope identification provided to a main connector when the scope is electrically connected to the apparatus body through the main connector.

4. An endoscopic apparatus as claimed in claim 1, wherein said apparatus further comprises a digital scan converter for memorizing an image, and inverting the image right and left, and controlling the image display.

5. An endoscopic apparatus as claimed in claim 1, wherein the adjustment of the change of the optical characteristics is to adjust the color of an image by changing the hue and saturation of the image.

6. An endoscopic apparatus as claimed in claim 5, wherein the color is adjusted by red, green and blue signals, and brightness and color difference signals.

7. An endoscopic apparatus as claimed in claim 5, wherein the image color is adjusted at a stage of a modulated signal provided by modulating a sine wave of a color difference signal.

8. An endoscopic apparatus as claimed in claim 5, wherein the image color is adjusted by changing a color vector of the hue by arbitrary amount and angle.

9. An endoscopic apparatus as claimed in claim 5, wherein the image color is adjusted by generating voltages or addresses related to changes of the hue and saturation.

10. An endoscopic apparatus as claimed in claim 5, wherein the hue and saturation of the image are controlled on the basis of an analog voltage corresponding to data for correction written in advance with respect to the image.

* * * * *